(12) United States Patent
Hodgkinson et al.

(10) Patent No.: US 9,055,944 B2
(45) Date of Patent: Jun. 16, 2015

(54) SURGICAL INSTRUMENT BUTTRESS ATTACHMENT

(71) Applicant: Covidien LP, Mansfield, MA (US)

(72) Inventors: Gerald Hodgkinson, Guilford, CT (US); Sally Carter, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 71 days.

(21) Appl. No.: 13/917,949

(22) Filed: Jun. 14, 2013

(65) Prior Publication Data

US 2013/0277411 A1    Oct. 24, 2013

Related U.S. Application Data

(63) Continuation of application No. 13/044,623, filed on Mar. 10, 2011, now Pat. No. 8,479,968.

(51) Int. Cl.
*A61B 17/068* (2006.01)
*A61B 17/072* (2006.01)
*A61B 17/115* (2006.01)
*A61B 17/3211* (2006.01)

(52) U.S. Cl.
CPC ......... *A61B 17/07292* (2013.01); *A61B 17/072* (2013.01); *A61B 17/115* (2013.01); *A61B 17/1155* (2013.01); *A61B 17/068* (2013.01); *A61B 17/3211* (2013.01); *A61B 2017/07257* (2013.01); *A61B 2017/07271* (2013.01)

(58) Field of Classification Search
CPC ........... A61B 17/07292; A61B 17/068; A61B 17/1155; A61B 2017/07257

USPC .......... 227/175.1, 176.1, 180.1; 606/219, 151
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,490,675 A | 1/1970 | Green et al. |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,485,816 A | 12/1984 | Krumme |
| 4,605,730 A | 8/1986 | Shalaby et al. |

(Continued)

FOREIGN PATENT DOCUMENTS

| | | |
|---|---|---|
| CA | 2 667 434 | 5/2008 |
| DE | 1 99 24 311 A1 | 11/2000 |

(Continued)

OTHER PUBLICATIONS

European Search Report corresponding to EP 05 02 2585.3, completed Jan. 25, 2006 and mailed Feb. 3, 2006; 4 pages.

(Continued)

*Primary Examiner* — Michelle Lopez

(57) ABSTRACT

A surgical stapler instrument has surgical stapler jaws, at least one staple line reinforcement material, and a fastener including a hook and a loop. The hook can be disposed on one of the surgical stapler jaws and the loop can be disposed on the staple line reinforcement material. Alternatively, the hook can be disposed on the staple line reinforcement material and the look on one of the surgical stapler jaws.

15 Claims, 6 Drawing Sheets

(56) References Cited

U.S. PATENT DOCUMENTS

| | | |
|---|---|---|
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,239,449 B2 | 7/2007 | Leitel et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson et al. |
| 8,167,895 B2 | 5/2012 | D'Agostino |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |

(56) References Cited

U.S. PATENT DOCUMENTS

| | | |
|---|---|---|
| 8,231,043 B2 | 7/2012 | Tarinelli |
| 8,235,273 B2 | 8/2012 | Olson et al. |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson et al. |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Stopek |
| 8,631,989 B2 | 1/2014 | Aranyi |
| 8,668,129 B2 | 3/2014 | Olson |
| 8,684,250 B2 | 4/2014 | Bettuchi |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, Iii et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0187179 A1 | 7/2012 | Gleiman |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |

(56) References Cited

U.S. PATENT DOCUMENTS

| | | | |
|---|---|---|---|
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi et al. |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |

FOREIGN PATENT DOCUMENTS

| | | | |
|---|---|---|---|
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A2 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 A1 | 8/2009 |
| EP | 2 090 244 | 8/2009 |
| EP | 2 090 252 | 8/2009 |
| EP | 2 198 787 A1 | 6/2010 |
| EP | 2 236 098 A2 | 10/2010 |
| EP | 2 236 099 | 10/2010 |
| EP | 2 311 386 | 4/2011 |
| EP | 2 436 348 | 4/2012 |
| EP | 2 462 880 | 6/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 106 | 7/2013 |
| EP | 2 630 922 | 8/2013 |
| EP | 2 644 125 | 10/2013 |
| JP | 2000-166933 | 6/2000 |
| JP | 2002-202213 | 7/2002 |
| JP | 2007-124166 | 5/2007 |
| WO | WO 90/05489 A1 | 5/1990 |
| WO | WO 95/16221 A1 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

European Search Report corresponding to EP 06 00 4598, completed Jun. 22, 2006; 2 pages.
European Search Report corresponding to EP 06 01 6962.0, completed Jan. 3, 2007 and mailed Jan. 11, 2007; 10 pages.
International Search Report corresponding to International Application No. PCT/US2005/036740, completed Feb. 20, 2007 and mailed Mar. 23, 2007; 8 pages.
International Search Report corresponding to International Application No. PCT/US2007/022713, completed Apr. 21, 2008 and mailed May 15, 2008; 1 page.
International Search Report corresponding to International Application No. PCT/US2008/002981, completed Jun. 9, 2008 and mailed Jun. 26, 2008; 2 pages.
European Search Report corresponding to EP 08 25 1779, completed Jul. 14, 2008 and mailed Jul. 23, 2008; 5 pages.
European Search Report corresponding to EP 08 25 1989.3, completed Mar. 11, 2010 and mailed Mar. 24, 2010; 6 pages.
European Search Report corresponding to EP 10 25 0639.1, completed Jun. 17, 2010 and mailed Jun. 28, 2010; 7 pages.
European Search Report corresponding to EP 10 25 0715.9, completed Jun. 30, 2010 and mailed Jul. 20, 2010; 3 pages.
European Search Report corresponding to EP 05 80 4382.9, completed Oct. 5, 2010 and mailed Oct. 12, 2010; 3 pages.
European Search Report corresponding to EP 10 25 1437.9, completed Nov. 22, 2010 and mailed Dec. 16, 2010; 3 pages.
European Search Report corresponding to EP 09 25 2897.5, completed Feb. 7, 2011 and mailed Feb. 15, 2011; 3 pages.
European Search Report corresponding to EP 10 25 0642.5, completed Mar. 25, 2011 and mailed Apr. 4, 2011; 4 pages.
European Search Report corresponding to EP 11 18 8309.6, completed Dec. 15, 2011 and mailed Jan. 12, 2012; 3 pages.
European Search Report corresponding to EP 12 15 2229.6, completed Feb. 23, 2012 and mailed Mar. 1, 2012; 4 pages.
European Search Report corresponding to EP 12 15 0511.9, completed Apr. 16, 2012 and mailed Apr. 24, 2012; 7 pages.
European Search Report corresponding to EP 12 15 2541.4, completed Apr. 23, 2012 and mailed May 3, 2012; 10 pages.
European Search Report corresponding to EP 12 16 5609.4, completed Jul. 5, 2012 and mailed Jul. 13, 2012; 8 pages.

(56) References Cited

OTHER PUBLICATIONS

European Search Report corresponding to EP 12 15 8861.0, completed Jul. 17, 2012 and mailed Jul. 24, 2012; 9 pages.
European Search Report corresponding to EP 12 16 5878.5, completed Jul. 24, 2012 and mailed Aug. 6, 2012; 8 pages.
Extended European Search Report corresponding to EP 12 19 1035.0, completed Jan. 11, 2013 and mailed Jan. 18, 2013; 7 pages.
Extended European Search Report corresponding to EP 12 18 6175.1, completed Jan. 15, 2013 and mailed Jan. 23, 2013; 7 pages.
Extended European Search Report corresponding to EP 12 19 1114.3, completed Jan. 23, 2013 and mailed Jan. 31, 2013; 10 pages.
Extended European Search Report corresponding to EP 12 19 2224.9, completed Mar. 14, 2013 and mailed Mar. 26, 2013; 8 pages.
Extended European Search Report corresponding to EP 12 19 6911.7, completed Apr. 18, 2013 and mailed Apr. 24, 2013; 8 pages.
Extended European Search Report corresponding to EP 12 19 6904.2, completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 13 15 6297.7, completed Jun. 4, 2013 and mailed Jun. 13, 2013; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).

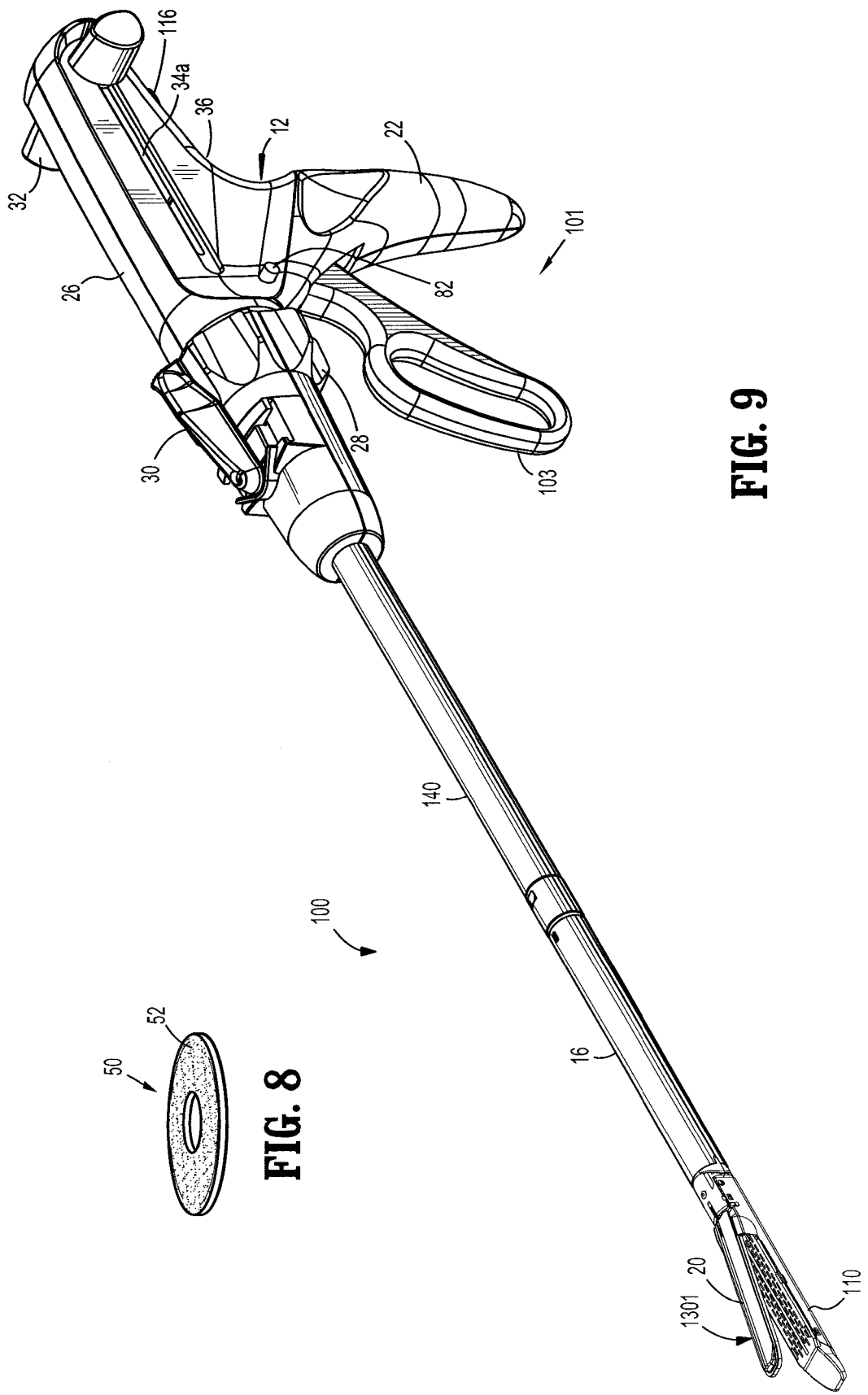

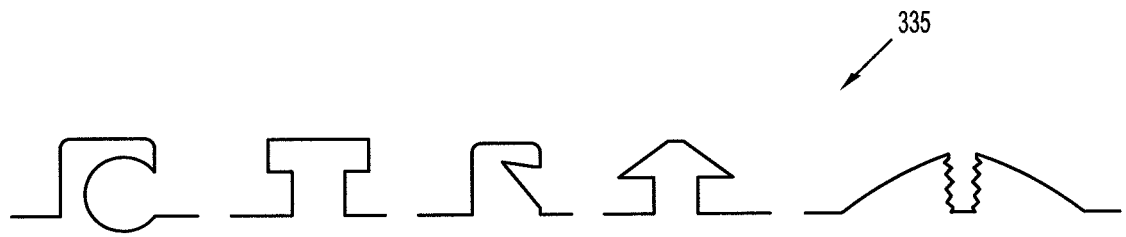
FIG. 15A  FIG. 15B  FIG. 15C  FIG. 15D  FIG. 15E
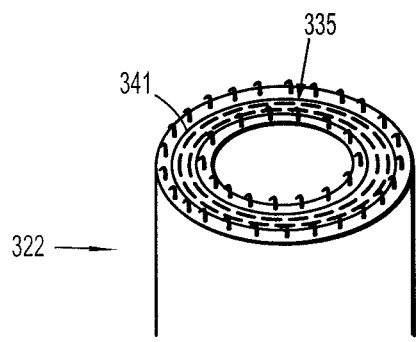
FIG. 16
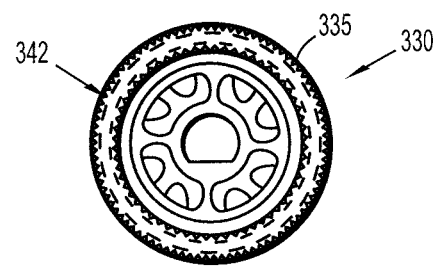
FIG. 17
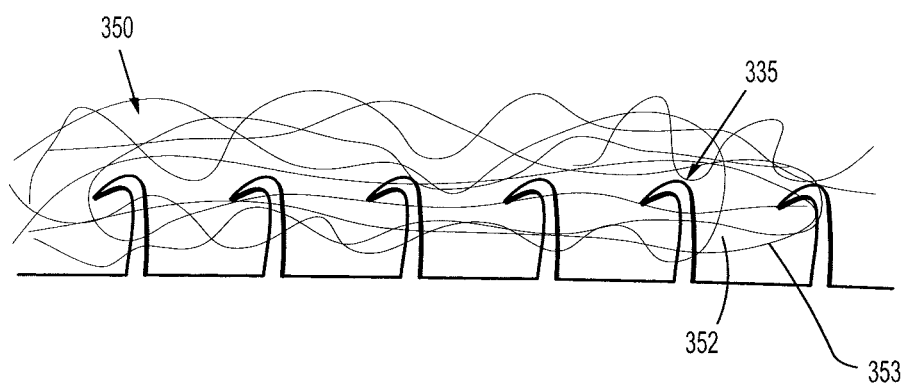
FIG. 18

SURGICAL INSTRUMENT BUTTRESS ATTACHMENT

CROSS-REFERENCE TO RELATED APPLICATIONS

This application is a Continuation of U.S. patent application Ser. No. 13/044,623 filed Mar. 10, 2011, the entire disclosure of which is incorporated by reference herein.

TECHNICAL FIELD

The present disclosure relates to a buttress attachment for a surgical instrument, such as a surgical stapler. More particularly, the buttress is attached to one or more of the working surfaces of the surgical instrument utilizing a fastener.

BACKGROUND

Buttresses for surgical instruments are known. Buttresses and/or staple line reinforcement materials include bioabsorbable, non-absorbable, synthetic and animal derived materials. Such buttress and/or staple line reinforcement materials are utilized to reduce the incidence of leaks and bleeding in a variety of surgical procedures. The use of staple line reinforcement material can reduce or eliminate suturing or clipping over staple lines and reduce the time for the surgical procedure.

Staple line reinforcement materials have been used with linear surgical staplers. The material can be provided in a tubular shape and slipped onto the surgical stapler jaw. In another approach, the staple line reinforcement material is attached to the working surface of the stapler utilizing pins. See U.S. Pat. No. 6,045,560 to McKean et al., and U.S. Pat. No. 5,503,638 et al., the disclosures of which are hereby incorporated by reference herein, in their entirety.

Buttress and/or staple line reinforcement materials have also been used with circular staplers. The staple line reinforcement material is attached to the working surface of the circular stapler utilizing protrusions at the perimeter of the staple line reinforcement material, the protrusions having adhesive for attaching the staple line reinforcement material to the working surfaces of the circular surgical stapler. After tissue sections are stapled together, the buttress material is attached to the tissue by the staples, with the tissue sandwiched between the staple line reinforcement material. In another approach, the staple line reinforcement material is attached to the shaft of the circular stapler. See Bauman et al., U.S. Pat. No. 7,547,312, U.S. Pat. No. 7,823,592, WO 03/082126, and WO 03/105698, the disclosures of which are hereby incorporated by reference herein, in their entirety.

One drawback to some of these approaches is that the knife of a surgical stapler instrument is relied upon to cut the staple line reinforcement material so that the instrument can be removed and the staple line reinforcement material remains with the staple line.

Drawbacks to some of these approaches include excess material that must be removed when the surgical instrument is withdrawn, as well as unreliable detachment of the staple line reinforcement material from the surgical instrument.

There is a desire for improved methods of attaching staple line reinforcement material to surgical instruments so that the instrument is packaged with the staple line reinforcement already installed, with a minimum of excess material, and a staple line reinforcement material that is reliably retained on the instrument while being detached from the instrument when the instrument is removed from the surgical site.

SUMMARY

In an aspect of the present disclosure, a surgical stapling instrument, comprising a handle assembly, a body portion, surgical stapling jaws, a staple line reinforcement material, and a fastener are disclosed. The body portion extends from the handle assembly and the surgical stapling jaws include a staple cartridge assembly and an anvil assembly disposed at the distal end of the body portion. The fastener has two parts, the two parts including a hook and a loop. At least one of the surgical stapling jaws has one of the hook and the loop, and the staple line reinforcement material has the other of the hook and the loop.

The anvil assembly has staple forming recesses and the cartridge assembly has staple receiving slots. The anvil assembly and the cartridge assembly may be arranged to form a circular staple line. Alternatively, the anvil assembly and the cartridge assembly may be arranged to form a linear staple line. The staple line reinforcement material can be a nonwoven, or the staple line reinforcement material can be a mesh, or other material.

In certain embodiments, the staple line reinforcement material has a plurality of pores. At least one of the surgical stapling jaws may have a plurality of hooks that are arranged to engage the plurality of pores.

In certain embodiments, the fastener includes a sheet having a plurality of hooks on a first side and an adhesive on a second side, the adhesive being attached to at least one of the surgical stapler jaws, and the staple line reinforcement material having a plurality of loops arranged to engage the plurality of hooks.

The anvil assembly and the cartridge assembly may be arranged to form a circular staple line and the instrument can further comprise a circular knife disposed inwardly of the circular staple line. The staple line reinforcement material can be circular in shape and have a central orifice.

In certain embodiments, the hook is disposed on at least one of the surgical stapler jaws and has a glass transition temperature at or near a human body temperature. The hook can be disposed on at least one of the surgical stapler jaws and have a glass transition temperature and the instrument can further comprise at least one thermistor for heating the hook to a temperature at or near the glass transition temperature.

In certain embodiments, the hook has a first base end and a second free end, a diameter of the first base end being greater than a diameter of the second free end so that the second free end is relatively flexible.

The staple line reinforcement material may have a plurality of fibers, at least one of the surgical stapler jaws having the hook, and the hook being arranged to engage one or more of the plurality of fibers.

In another aspect of the present disclosure, a surgical stapling instrument comprises a handle assembly, a body portion extending from the handle assembly, surgical stapling jaws including a staple cartridge assembly and an anvil assembly disposed at the distal end of the body portion. The staple cartridge assembly has a first tissue contacting surface and the anvil assembly having a second tissue contacting surface. A plurality of hooks is attached to at least one of the first tissue contacting surface and the second tissue contacting surface. A staple line reinforcement material is in engagement with at least some of the plurality of hooks.

The staple line reinforcement material may define a plurality of pores, the plurality of hooks being arranged to engage the staple line reinforcement material in the plurality of pores.

The staple line reinforcement material may be non-woven. Alternatively, the staple line reinforcement material is a mesh or other material.

In certain embodiments, the fastener includes a sheet having a plurality of hooks on a first side and an adhesive on a second side.

The anvil assembly has staple forming recesses and the cartridge assembly has staple receiving slots. The anvil assembly and the cartridge assembly may be arranged to form a circular staple line. Alternatively, the anvil assembly and the cartridge assembly may be arranged to form a linear staple line.

The anvil assembly and the cartridge assembly may be arranged to form a circular staple line and the instrument can further comprise a circular knife disposed inwardly of the circular staple line. The staple line reinforcement material can be circular in shape and have a central orifice.

In certain embodiments, the hooks have has a glass transition temperature at or near a human body temperature. The hooks can be disposed on at least one of the surgical stapler jaws and have a glass transition temperature and the instrument can further comprise at least one thermistor for heating the hooks to a temperature at or near the glass transition temperature.

In certain embodiments, the hooks have a first base end and a second free end, a diameter of the first base end being greater than a diameter of the second free end so that the second free end is relatively flexible.

In a further aspect of the present disclosure, a surgical stapling instrument comprises a handle assembly, a body portion extending from the handle assembly, surgical stapling jaws including a staple cartridge assembly and an anvil assembly disposed at the distal end of the body portion. The staple cartridge assembly has a first tissue contacting surface and the anvil assembly having a second tissue contacting surface. At least one of the first tissue contacting surface and the second tissue contacting surface has a plurality of hooks. A staple line reinforcement material is in engagement with at least some of the plurality of hooks.

The staple line reinforcement material may include a plurality of fibers, the plurality of hooks being arranged to engage at least some of the plurality of fibers of the staple line reinforcement material. The staple line reinforcement material may be non-woven. Alternatively, the staple line reinforcement material is a mesh.

In certain embodiments, the instrument has a sheet having a plurality of hooks on a first side and an adhesive on a second side.

The anvil assembly has staple forming recesses and the cartridge assembly has staple receiving slots. The anvil assembly and the cartridge assembly may be arranged to form a circular staple line. Alternatively, the anvil assembly and the cartridge assembly may be arranged to form a linear staple line.

The anvil assembly and the cartridge assembly may be arranged to form a circular staple line and the instrument can further comprise a circular knife disposed inwardly of the circular staple line. The staple line reinforcement material can be circular in shape and have a central orifice.

In certain embodiments, the hooks have a glass transition temperature at or near a human body temperature. The hooks can be disposed on at least one of the surgical stapler jaws and have a glass transition temperature and the instrument can further comprise at least one thermistor for heating the hooks to a temperature at or near the glass transition temperature.

In certain embodiments, the hooks have a first base end and a second free end, a diameter of the first base end being greater than a diameter of the second free end so that the second free end is relatively flexible.

In a further aspect of the present disclosure, a surgical stapling instrument comprises a handle assembly, a body portion extending from the handle assembly, surgical stapling jaws including a staple cartridge assembly and an anvil assembly disposed at the distal end of the body portion. The staple cartridge assembly has a first tissue contacting surface and the anvil assembly having a second tissue contacting surface. The instrument includes a sheet having an adhesive at a first side of the sheet and at the second side of the sheet. At least one of the first tissue contacting surface and the second tissue contacting surface has the first side of the sheet attached thereto so that the second side of the sheet is accessible for placement of a staple line reinforcement material thereon. In certain embodiments, the first tissue contacting surface defines rows of staple receiving slots the sheet is attached outwardly of rows of staple receiving slots. In certain embodiments, the first tissue contacting surface defines annular rows of staple receiving slots and the sheet is attached outwardly of the rows of staple receiving slots. Additionally or alternatively, the first tissue contacting surface defines annular rows of staple receiving slots and the sheet is attached inwardly of the rows of staple receiving slots. In certain embodiments, one or more sheets are attached to the second tissue contacting surface. In certain embodiments, the adhesive of the first side of the sheet is selected to so as to maintain the sheet attached to the at least one of the first tissue contacting surface and the second tissue contacting surface as the instrument is removed from a surgical site. The adhesive of the second side of the sheet is selected so as to allow the staple line reinforcement material to be released from the sheet.

BRIEF DESCRIPTION OF THE DRAWINGS

The accompanying drawings, which are incorporated in and constitute a part of this specification, illustrate embodiments of the present disclosure and, together with a general description of the disclosure given above and the detailed description of the embodiments given below, serve to explain the principles of this disclosure, wherein:

FIG. 8 is a perspective view of a staple line reinforcement material in accordance with the embodiment of FIGS. 1 through 5 and 7;

FIG. 9 is a perspective view of a surgical stapler instrument according to another embodiment of the present disclosure;

FIGS. 15a through 15e are cross-sectional views of engaging features formed on one or more tissue contacting surfaces of a surgical stapling instrument in accordance with another embodiment of the present disclosure;

FIG. 16 is a perspective view of a tissue contacting surface of a cartridge assembly according to the embodiment of FIGS. 15a through 15e;

FIG. 17 is a plan view of a tissue contacting surface of an anvil assembly according to the embodiment of FIGS. 15a through 16; and FIG. 18 is a view in elevation of a staple line reinforcement material attached to a plurality of hooks in accordance with the embodiment of FIG. 15a through FIG. 17.

DETAILED DESCRIPTION

Figure 1:
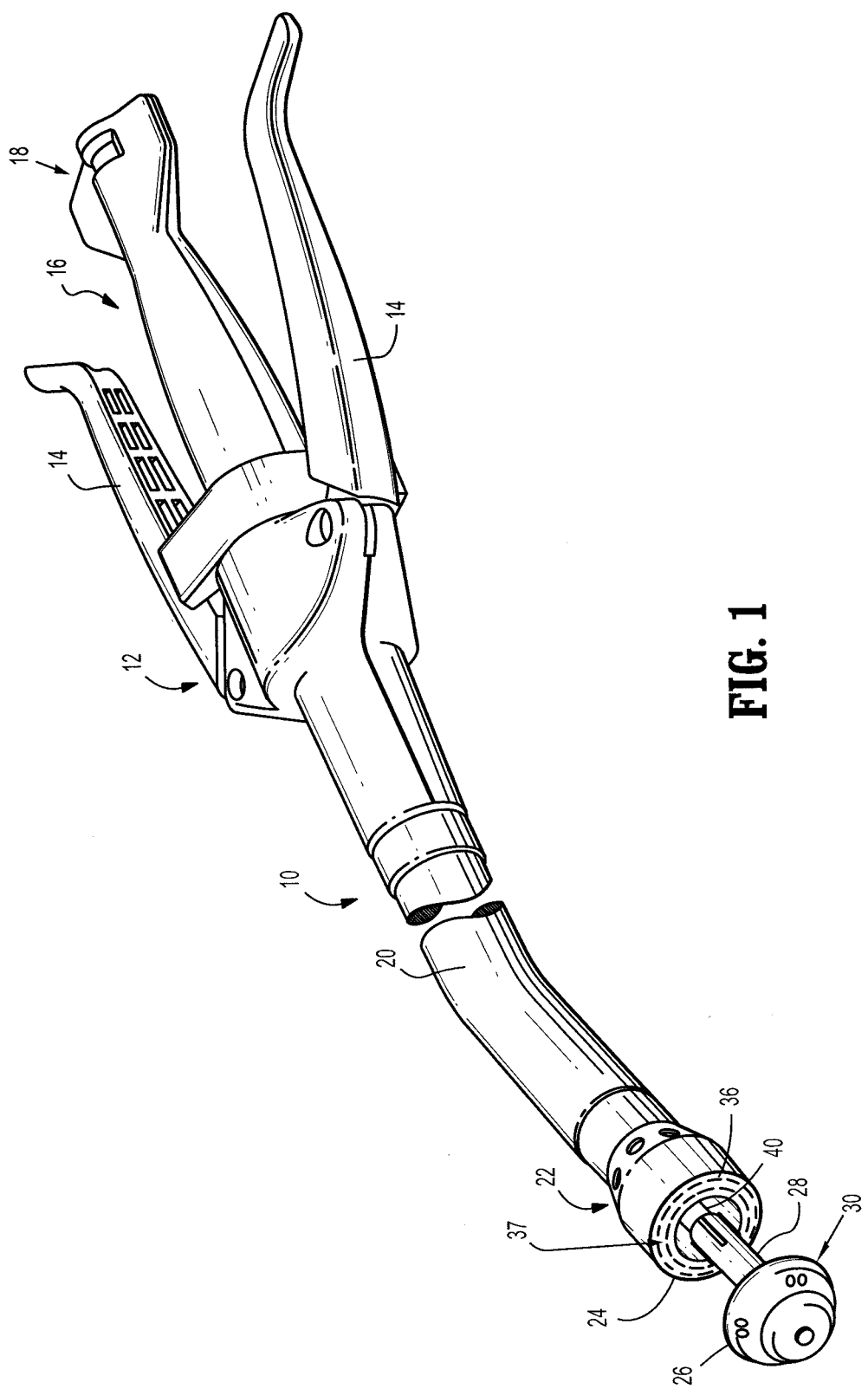
FIG. 1 is a perspective view of a surgical stapler instrument according to an embodiment of the present disclosure.

Embodiments of the presently disclosed devices and structures will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

FIG. 1 illustrates a circular surgical stapling instrument which is generally designated as 10. Surgical stapling device 10 includes a handle assembly 12 having at least one pivotable actuating handle 14 and a rotatable actuator 18. A tubular body portion 20 extends from the handle assembly 12. The tubular body portion 20, which generally has a circular cross-sectional shape, may have a straight or a curved shape along its length and may be flexible or relatively rigid. Cross-sectional shapes other that circular are contemplated, so that the tubular body portion 20 can have a polygonal, elliptical, semi-circular, ovoid, or other shape. Surgical stapling jaws including a staple cartridge assembly and an anvil assembly are disposed at a distal end of the body portion. The body portion 20 terminates in a staple cartridge assembly 22 that has a tissue contacting surface defining one or more rows 37 of staple receiving slots 36. Each staple receiving slot has a staple (not shown) disposed therein. Typically, a pair of circular rows 37 of staple receiving slots 36 is provided, although other shapes, such as annular, are contemplated. An anvil assembly 30 is positioned distally of the staple cartridge assembly 22, which includes an anvil member 26 and a shaft 28 operatively associated therewith. The anvil assembly has a tissue contacting surface that defines staple forming recesses that correspond to the circular rows of staple receiving slots, so that the stapling instrument forms circular staple lines. The tubular body portion 20 has a corresponding rod or shaft 40 centrally located with respect to the staple cartridge assembly 22. The shaft 28 is removably connectable to the shaft 40 of the tubular body portion 20.

The staple cartridge assembly 22 is connectable to the distal end of tubular body portion 20 or may be configured to concentrically fit within the distal end of tubular body portion 20. Typically, staple cartridge assembly 22 includes a staple pusher (not shown) with a distal portion defining two concentric rings of peripherally spaced fingers (not shown), each one of which is received within a respective staple receiving slot 36.

Typically, a knife (not shown) having a cutting edge is disposed within the staple cartridge assembly 22. The knife edge is circular and disposed radially inward of the rows of staples. The knife is mounted so that as the staple pusher is advanced axially in the direction of the anvil assembly, the knife is also advanced axially. The staple pusher is advanced in the distal direction to drive staples from the staple receiving slots 36 against the anvil member so that the staple forming recesses form the staples in a closed shape. As the pusher is advanced, the knife is advanced and driven toward the anvil assembly 30 to cut tissue.

U.S. Pat. No. 5,915,616 to Viola et al., the entire content of which is hereby incorporated by reference herein in its entirety, discloses a circular stapling device. Although a circular stapling apparatus is shown in FIG. 1, the stapling device may be arranged to deploy staples in a semi-circular or other desired shape. Although discussed with reference to intestinal tissue, devices according to the present disclosure can be arranged to join and/or treat other tissues in other procedures.

Figure 2:
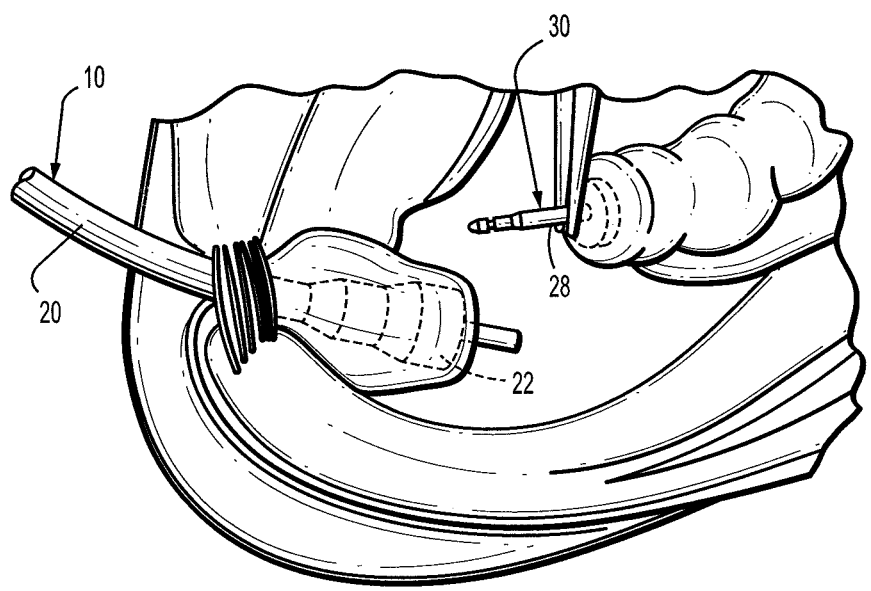
FIG. 2 is a perspective view of an anvil assembly and staple cartridge assembly according to the embodiment of FIG. 1.
Figure 3:
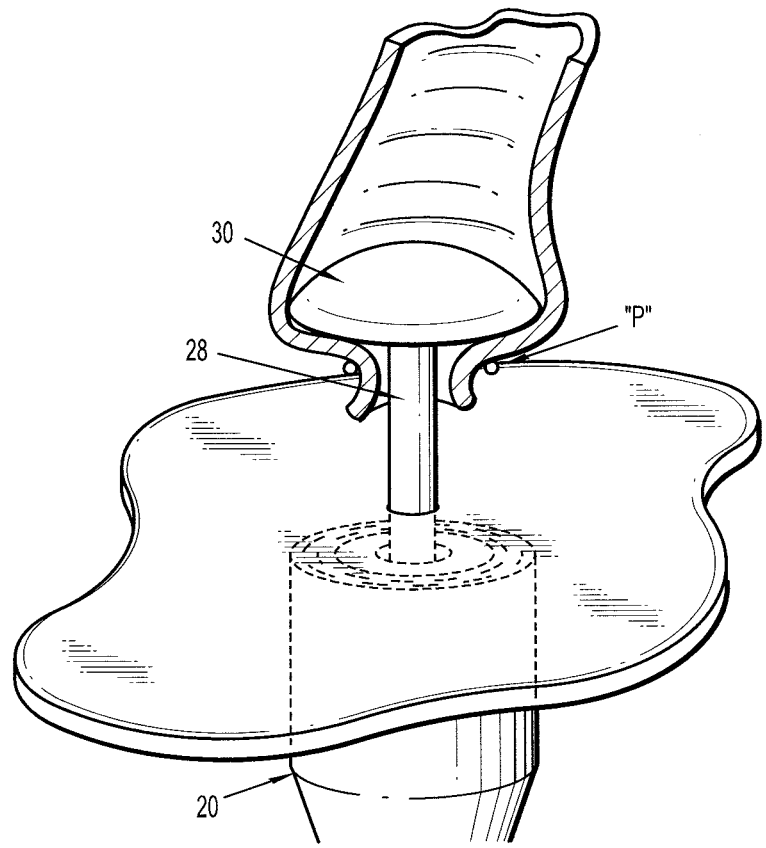
FIG. 3 is a perspective view of an anvil assembly and staple cartridge assembly according to the embodiment of FIGS. 1 and 2.

As shown in FIGS. 2 and 3, the anvil assembly 30 is detached from the rod or shaft 40 of the tubular body portion 20 and a section of tubular body vessel, such as a section of intestine, is secured to the anvil assembly 30, typically by tying a suture "P" around the shaft 28 of the anvil assembly 30. Another section of tubular tissue is secured to the tubular body portion 20 by tying a suture around the shaft 40. See FIG. 2. The shaft 28 is then connected to the shaft 40. The actuator 18 is rotated to withdraw the shafts 28, 40 thereby approximating the anvil assembly 30 with the staple cartridge assembly 22. To fire the staples, the handles 14 are squeezed, which advances the staple pusher and the knife (not shown). The staples pass through each section of tubular tissue and are formed against the anvil so that the sections of tubular tissue are joined to one another. The knife cuts the tissue radially inward of the rows of staples, and the sutured material is removed with the circular stapling device.

Disclosed herein is a surgical stapling instrument 10, and staple line reinforcement material 50 fastened thereto. The surgical stapling instrument has surgical stapling jaws comprising the anvil assembly 30 and the staple cartridge assembly 22, each having a tissue contacting surface that engages the tissue. The tissue contacting surface 41 of the staple cartridge assembly 22 defines the staple receiving slots 36, whereas the tissue contacting surface 42 of the anvil assembly 30 defines staple forming recesses 31.

A staple line reinforcement material ("SLRM") 50 can be attached to the surface 41, the surface 42, or both. Desirably, the SLRM 50 is attached to one or more tissue contacting surfaces before the surgical stapling instrument is packaged, so that the surgeon and/or operating room personnel are not required to install the SLRM onto the surgical stapling instrument before the surgery. However, installation of the SLRM just prior to the surgery is also contemplated.

Figure 7:
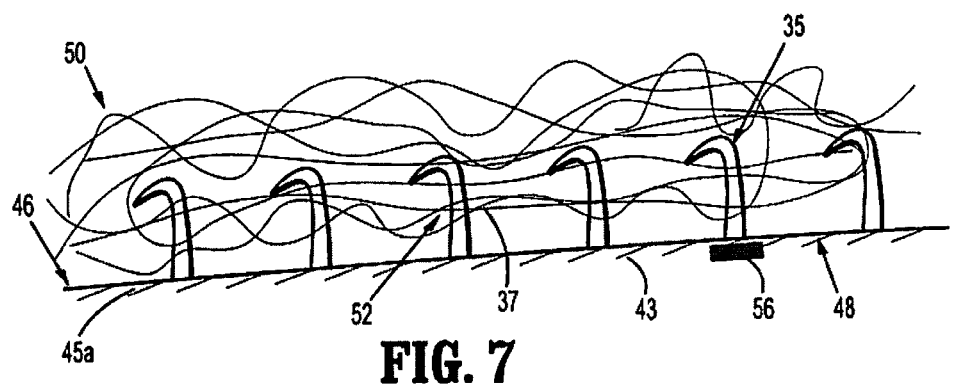
FIG. 7 is a view in elevation of a staple line reinforcement material attached to a plurality of hooks in accordance with the embodiment of FIGS. 1 through 5.

The SLRM 50 and the surgical stapling instrument 10 define a fastener 32 having two parts. The first part is a hook, or a plurality of hooks 35, and the second part is a loop, or a plurality of loops 37. The hook or hooks 35 can be provided on the surgical stapler jaw and the loop or loops 37 can be provided on the SLRM 50. Alternatively, the hook or hooks are provided on the SLRM and the loop or loops are provided on the surgical stapler jaws. See FIG. 7.

In certain preferred embodiments, the SLRM 50 comprises a material having a plurality of pores 52 and the hooks 35 comprises fiber hooks that are applied to the surface 41 of the staple cartridge assembly 22 and to the surface 42 of the anvil assembly 30. The hooks can be formed from a polymer, metallic materials such as steel, etc. The hooks engage the SLRM in the pores. The pores can be formed as apertures in a sheet of material, or recesses, or the pores can comprise openings defined between fibers, threads wires, etc. that makeup the SLRM.

Figure 4:
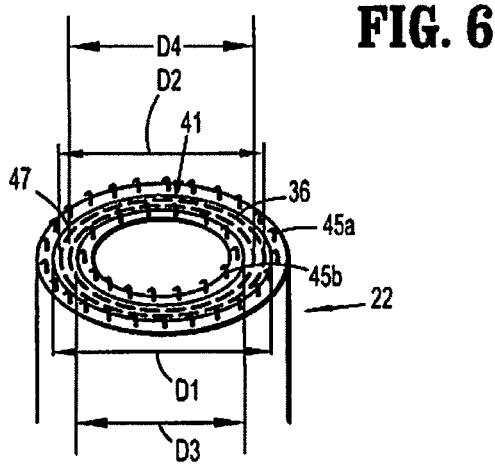
FIG. 4 is a perspective view of a tissue contacting surface of a cartridge assembly according to the embodiment of FIGS. 1 through 3.

A sheet 45*a* having a plurality of fiber hooks 35*a* on a first side 46 and an adhesive material 43 on a second side 48 is applied to the working surface 41 of the staple cartridge assembly 22. The sheet 45*a* is circular in shape and has a central orifice 47 with a diameter D1. The diameter D1 is larger than an outer diameter D2 of the rows 37 of staple receiving slots 36. Another sheet 45*b* has hooks 35 and is circular in shape and has an outer diameter that is smaller than an inner diameter D4 of the rows 37 of staple receiving slots 36. Each of the sheets 45*a* and 45*b* are adhered to the working surface 41 so that they do not overly the staple receiving slots 36. See FIGS. 4 and 7. The adhesive material is selected so that the adherence of the sheet to the instrument is strong enough so that the sheet is retained with the instrument after the staples have been fired and the tissue has been cut.

Figure 5:
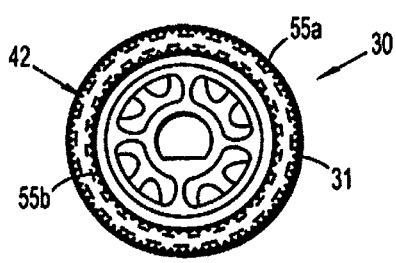
FIG. 5 is a perspective view of a tissue contacting surface of an anvil assembly according to the embodiment of FIGS. 1 through 4.

A sheet 55*a* having a first side with an adhesive material and a second side having a plurality of fiber hooks is attached to the working surface 42 of the anvil assembly 30 so that the sheet 55*a* lies outwardly of the staple forming recesses 31. Another sheet 55*b* with a first side having an adhesive material and a second side with a plurality of loops is attached to the working surface 42 of the anvil assembly 30 so that it lies inwardly of the staple forming recesses. See FIG. 5.

The SLRM 50 is a circular piece of porous material having a central orifice for accommodating the shaft 28 and shaft 40. See FIG. 8. The SLRM 50 is applied to the working surface 41 and the working surface 42 by pressing the SLRM 50 against the hooks 35 on the working surfaces 41 and 42. The hooks 35 engage the SLRM 50 in the pores 52 thereby retaining the SLRM 50 against the working surface 41 of the staple cartridge assembly 22 and the working surface 42 of the anvil assembly 30. The SLRM 50 is sized to overlie the working surfaces of the staple cartridge assembly 22 and the anvil assembly 30. The SLRM 50 and the sheets 45*a*, 45*b*, 55*a*, 55*b* do not interfere with the operation of the pusher or the knife, as the SLRM has a central orifice 51 that has a diameter that is larger than the diameter of the knife.

It is contemplated that the area of attachment, hook density, hook fiber strength, hook fiber length, and the pressing of the SLRM onto the hooks can be optimized to ensure retention of the SLRM and also easy release of the SLRM after the surgical stapling instrument is fired.

It is contemplated that the SLRM 50 may be fabricated from or include a surgical grade, biocompatible, non-absorbable material and may comprise a mesh. For example, the SLRM 50 may be fabricated from "TEFLON", which is a registered trademark owned by DuPont de Nemours & Co. It is further contemplated that body portion 102 may be fabricated from a biocompatible polymeric foam, felt, polytetrafluoroethylene (ePTFE), gelatin, fabric or the like, or any other biocompatible material.

Non-absorbable materials used for SLRM include, and are not limited to, those that are fabricated from such polymers as polyethylene, polypropylene, nylon, polyethylene terephthalate, polytetrafluoroethylene, polyvinylidene fluoride, and the like. Further non-absorbable materials include and are not limited to stainless steel, titanium and the like.

In one embodiment, the SLRM 50 may be fabricated from a bio-absorbable material. In other embodiments, the SLRM has at least one portion that is absorbable and at least one portion that is not absorbable. Bio-absorbable materials used for SLRM include, and are not limited to, those fabricated from homopolymers, copolymers or blends obtained from one or more monomers selected from the group consisting of glycolide, glycolic acid, lactide, lactic acid, p-dioxanone, α-caprolactone and trimethylene carbonate. Other bio-absorbable materials include and are not limited to, for example, Polyglycolic Acid (PGA) and Polylactic Acid (PLA). In one embodiment, the SLRM may be fabricated from bio-absorbable felt, gelatin or any other bio-absorbable materials.

The SLRM 50 can incorporate a wound treatment material "W", which includes and is not limited to one or a combination of adhesives, hemostats, sealants, coagulants, astringents, and medicaments. Other surgically biocompatible wound treatment materials "W" which may be employed in or applied by surgical instruments, including surgical staplers, include adhesives whose function is to attach or hold organs, tissues or structures; sealants to prevent fluid leakage; hemostats to halt or prevent bleeding; coagulants, astringents (e.g., sulfates of aluminum) and medicaments. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. The W can include medicaments. Medicaments may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

The SLRM may include a single layer including a homogeneous array of bio-absorbable or non-absorbable materials or a heterogeneous array of bio-absorbable and/or non-absorbable materials. The SLRM may include a layered body portion having at least two layers as indicated by first layer, film or wafer and second layer, film or wafer. In this embodiment, each layer may include a homogeneous or heterogeneous array of bio-absorbable and/or non-absorbable materials.

In certain preferred embodiments, the SLRM is a non-woven fabric. The non-woven fabric can be formed utilizing a melt blown process, including the following steps. The polymer resin is melt extruded. A melt pump meters out the molten polymer to a die head having an array of holes. By way of example, the holes have a diameter of between about 0.175 and about 0.25 millimeters. The polymer is forced through the array of holes in the die. Polymer fibers exit the die and are forced onto a conveyor belt. A stream of blowing hot air can be used to force the polymer fibers onto the conveyor. Suction through the conveyor belt surface can be used to compact the fibers against the belt and against each other, as the fibers cool. Additional compression may be applied to the fibers, such as by using a calendaring roll, which may include heating or cooling. The non-woven fabric may then be annealed. For example, isometric tension or other uniform compression can be used to drive crystallization and remove the monomer. The polymer is desirably a bioabsorbable or non-bioabsorbable polymer, such as a glycolide lactide copolymer (the material utilized in Polysorb™ sutures), a termpolymer composed of glycolide, trimethylene carbonate and dioxanone (the material utilized in Biosyn™ sutures), a polymer of glycolide, caprolactone, trimethylene carbonate, and lactide (the material utilized in Caprosyn™ sutures), and a glycolide trimethylene carbonate copolymer (the material utilized in Maxon™ sutures).

In certain embodiments, the non-woven fabric is porous. For example, the non-woven fabric can have a porosity of between about 50% and about 90%. The fiber diameter may be between about 5 and about 100 μm. The fabric thickness may be between about 150 and about 400 μm.

In other embodiments of the present disclosure, the SLRM 50 has the hooks 35 disposed on a surface thereof, and the loops 39 are attached to the tissue contacting surface 41 and/or tissue contacting surface 42.

In certain embodiments, the sheets 45a, 45b, 55a, and/or 55b, or the SLRM 50, have hooks 35 are fabricated from a polymer having a glass transition temperature at or near a human body temperature. When the surgical stapler instrument is utilized in the body, the stapler jaws will be approximated with one another to clamp on tissue. The hooks will warm and soften so that the SLRM 50 is more easily removed after the staples have been fired, but the hooks 35 are initially relatively rigid to retain the material 50 on the surgical stapler instrument 10. The surgical instrument can include thermistors for heating the hooks so that they soften when heated at some predetermined temperature which may be below or above body temperature.

In a further embodiment, the hooks 35 discussed above are formed of a shape memory polymer with shape shifting capacity at about 50 degrees Centigrade. Alternatively, the surgical stapler instrument 10 can include thermistors for heating the hooks 35 above 50 degrees Centigrade. Alternatively, the heat of a human body (about 37 Centigrade) could alter the shape of the shape memory polymer hooks to allow easier release of the SLRM 50. The heating of the hooks 35 causes a change in shape that allows the SLRM to be more easily removed from the surgical stapler instrument 10. For example, the heating can cause the hooks 35 to change from a hook configuration to a straight, or substantially straight, configuration.

Figure 6:
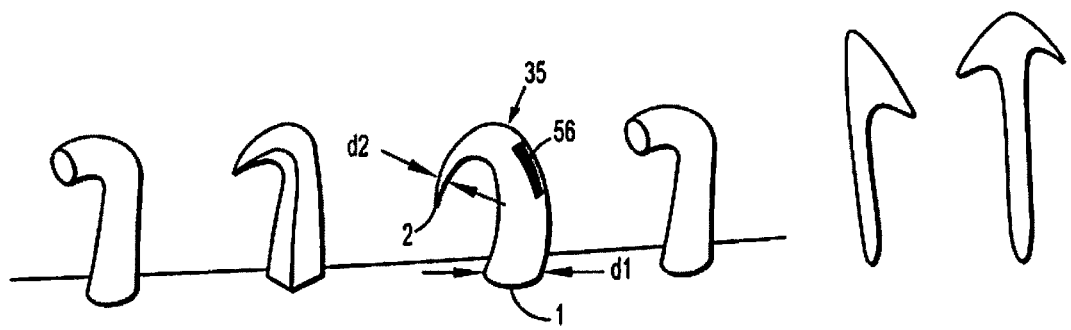
FIG. 6 is a perspective view of a plurality of hooks in accordance with further embodiments of the present disclosure.

In a further embodiment, any of the hooks 35 discussed above has a first base end 1 and a second free end 2. A diameter "d1" of the first base end is greater than a diameter "d2" of the second free end so that the second free end is relatively flexible. The base end is relatively stiff. See FIG. 7. The geometry of the hooks 35 is tailored so that the lifting force is reduced and the SLRM will be released more easily after the surgical stapler instrument is fired. The hooks 35 can have a variety of shapes, including polygonal, tubular, tapering, arrow-shaped, etc. See FIG. 6.

In a further embodiment, the surgical instruments discussed herein have a staple line reinforcement material has a plurality of fibers and at least one of the surgical stapler jaws has the hooks 35. The hooks are arranged to engage one or more of the plurality of fibers to releasably retain the SLRM on the stapler jaws.

FIG. 9 illustrates a linear stapling instrument 100 having stapler jaws 110, 120. The stapler jaw 110 is a staple cartridge assembly having one or more rows 137 of staple receiving slots 136. Each staple receiving slot has a staple (not shown) disposed therein. Typically, three linear rows 137 of staple receiving slots 136 are provided on either side of a channel 139. An anvil assembly 130 is positioned in opposition to the staple cartridge assembly 122 and pivotably mounted so that the anvil assembly and staple cartridge assembly can be approximated to clamp tissue therebetween. The anvil assembly includes an anvil member 126 defining a plurality of staple forming recesses 131 that correspond to the linear rows 137 so that the stapling instrument forms linear staple lines. The stapling jaws 110, 120 are disposed at a distal end of an endoscopic shaft 140. A handle assembly 101 includes a pivotable handle 103 that drives movement of a drive member through the staple cartridge assembly 122. The drive member (not shown) passes through the channel 139 and pushes a sled or camming bar through the staple cartridge to drive staple pushers, and the staples, through the slots 136 toward the staple forming recesses of the anvil member 126. Such a surgical instrument is disclosed in U.S. Pat. No. 6,241,139 to Milliman et al., the disclosure of which is hereby incorporated by reference herein, in its entirety.

The stapling instrument has a staple line reinforcement material 150 fastened thereto. The staple cartridge assembly 122 and the anvil assembly 130 each have a tissue contacting surface that engages the tissue. The tissue contacting surface 141 of the staple cartridge assembly 122 defines the staple receiving slots 136, whereas the tissue contacting surface 142 of the anvil assembly 130 defines staple forming recesses 131.

Figure 12:
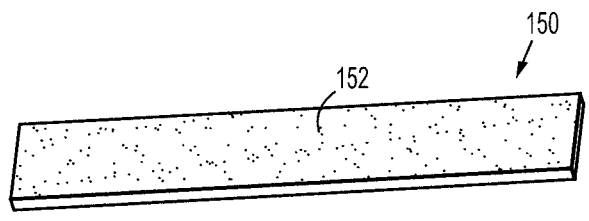
FIG. 12 is a perspective view of a staple line reinforcement material in accordance with the embodiment of FIGS. 9 through 11.
Figure 13:
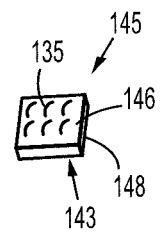
FIG. 13 is a perspective view of a sheet in accordance with the embodiment of FIGS. 9 through 12.

A SLRM 150 can be attached to the surface 141, the surface 142, or both. See FIG. 12. Desirably, the SLRM 150 is attached to one or more tissue contacting surfaces before the surgical stapling instrument is packaged, so that the surgeon and/or operating room personnel are not required to install the SLRM onto the surgical stapling instrument before the surgery. However, installation of the SLRM just prior to the surgery is also contemplated.

The SLRM 150 and the surgical stapling instrument 110 define a fastener 132 having two parts. The first part is a hook, or a plurality of hooks 135, and the second part is a loop, or a plurality of loops 137. The hook or hooks 135 can be provided on the surgical stapler jaw and the loop or loops 137 can be provided on the SLRM 150. Alternatively, the hook or hooks are provided on the SLRM and the loop or loops are provided on the surgical stapler jaws.

Figure 10:
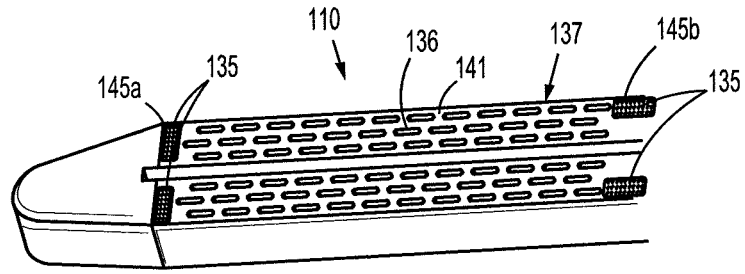
FIG. 10 is a perspective view of the tissue contacting surface of a staple cartridge assembly in accordance with the embodiment of FIG. 9.

In certain preferred embodiments, the SLRM 150 comprises a material having a plurality of pores 152 and the hooks 135 comprise fiber hooks that are applied to the surface 141 of the staple cartridge assembly 22 and/or to the surface 142 of the anvil assembly 130. The hooks can be formed from a polymer, a metallic material such as steel, etc. A sheet 145 having a plurality of fiber hooks 135 on a first side 146 and an adhesive material 143 on a second side 148 is applied to the tissue contacting surface 141 of the staple cartridge assembly 122. The sheet 145 is generally rectangular or oblong in shape and lies outside the rows 137 of staple receiving slots. For example, at least one first sheet 145a is disposed at a distal end of the working surface 141 and at least one second sheet 145b is disposed at a proximal end of the working surface 141. The sheets 145 are adhered to the working surface 141 so that they do not overly the staple receiving slots 136. See FIG. 10.

Figure 11:
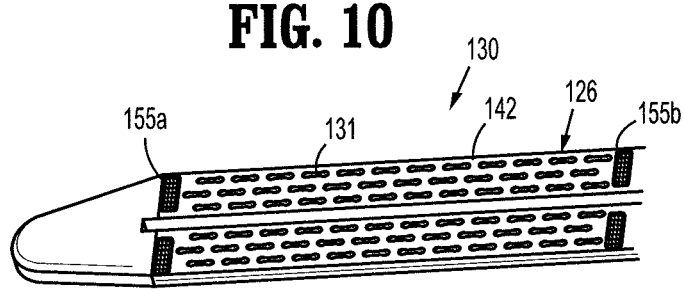
FIG. 11 is a perspective view of the tissue contacting surface of an anvil assembly in accordance with the embodiment of FIGS. 9 and 10.

At least one first sheet 155a having a first side with an adhesive material and a second side having a plurality of fiber hooks is attached to the tissue contacting surface 142 of the anvil assembly 130, at a distal end of the surface 142. At least one second sheet 155b is also attached at the proximal end of the surface 142. The sheets lie outwardly of the staple forming recesses 131. See FIG. 11.

The SLRM 150 is a generally rectangular piece of porous material. A SLRM 150 is applied to each of the surface 141 and the surface 142 by pressing a SLRM 150 against the hooks 135 on the tissue contacting surface 141 and pressing another SLRM against the hooks on the tissue contacting surface 142. The hooks 135 engage the SLRM 150 in the pores 152 thereby retaining the SLRM 150 against the working surface 141 of the staple cartridge assembly 122 and the working surface 142 of the anvil assembly 130. The SLRM 150 is sized to overlie the working surfaces of the staple cartridge assembly 122 and the anvil assembly 130. The SLRM 150 and the sheets 145, 155 do not interfere with the operation of the pusher or the knife. The knife, which is carried by the drive member of the stapling instrument 100, divides the SLRM, separating the SLRM into two parts.

In another embodiment, the SLRM 150 is attached to the surface 141, the surface 142, or both utilizing a sheet (145, 155) that is elongate in shape and extends alongside the rows 137 of staple receiving slots 136, the staple forming recesses 131, or both. One or more elongate sheets can be applied to the surface 141 and/or surface 142. Hooks 135 on the sheet or sheets attach the SLRM to the surface 141 and/or surface 142.

SLRM 150 comprises a material having a plurality of pores 152. Alternatively, the SLRM 150 comprises a material having a plurality of fibers, or any of the other materials discussed above. The hooks 135 that are attached to surface 141 and surface 142 engage the SLRM in the pores or the fibers of the SLRM, as discussed above.

It is contemplated that the area of attachment, hook density, hook fiber strength, hook fiber length, and the pressing of the SLRM onto the hooks can be optimized to ensure retention of the SLRM and also easy release of the SLRM after the surgical stapling instrument is fired.

In a further embodiment, the surgical stapling instrument 100 has surgical stapling jaws, a staple line reinforcement material, and an attachment sheet 245 having a first side 246 and a second side 248 with an adhesive thereon. The SLRM 50 is attached to the first side 246 by the adhesive and the second side 248 is attached to the tissue contacting surface of at least one of the circular surgical stapling jaws. The surgical stapling jaws include an anvil assembly and a cartridge assembly. In certain embodiments, the anvil assembly and the cartridge assembly are arranged to form a circular staple line. In other embodiments, the anvil assembly and the cartridge assembly are arranged to form a linear staple line.

Figure 14:
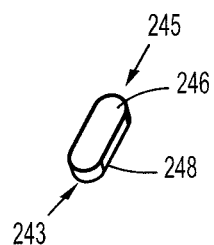
FIG. 14 is a perspective view of a sheet in accordance with a further embodiment of the present disclosure.

The attachment sheet 245, as depicted in FIG. 14, has a rectangular or oblong shape and one or more attachment sheets 245 can be placed on the working surface 41 of the staple cartridge assembly 22 to attach the SLRM to the working surface 41. In certain embodiments, the sheet or sheets 245 are placed outwardly of the rows 37 of staple receiving slots 36 defined by the surface 41 and may also be placed inwardly of the rows 37 of staple receiving slots 36. In other embodiments, the attachment sheet is circular in shape, with an orifice that is dimensioned to be larger than the staple retaining slots or staple forming recesses. Another sheet dimensioned to be smaller than the slots and/or rows can be used.

One or more attachment sheets can be placed on the tissue contacting surface 42 of the anvil assembly 30 to attach the SLRM to the surface 42. In certain embodiments, the sheet or sheets 245 are placed outwardly of the staple forming recesses 31 defined by the working surface 42 and may also be placed inwardly of the staple forming recesses 31 to attach a SLRM to the anvil assembly.

In a further embodiment, the sheet 245 having a first side 246 and a second side 248 with an adhesive thereon can be attached to the working surface 141 and/or working surface 142. The SLRM 150 is attached to the first side 246 by the adhesive and the second side 248 is attached to the working surface of at least one of the surgical stapling jaws. The adhesive on the first side 246 is selected to allow the SLRM to be released from the instrument after firing of staples and cutting of tissue so that the SLRM will remain with the stapled tissue and the instrument can be removed. Conversely, the second side has an adhesive that is selected to maintain the sheet 245 attached to the instrument as the instrument is removed. The adhesive sheet 245 can be used with instrument 10 or instrument 100 discussed above, or other surgical stapling instruments.

In another embodiment, the SLRM 150 is attached to the working surface 141, the working surface 142, or both utilizing a sheet (145, 155) that elongate in shape and extends alongside the rows 137 of staple receiving slots 136, the staple forming recesses 131, or both. One or more elongate sheets can be attached to the working surface 142 and/or working surface 142 by adhesive and the SLRM can be attached to the sheet or sheets by adhesive.

In a further embodiment, the surgical stapling instrument 10 or the surgical stapling instrument 100, or another stapling instrument, has a handle assembly, a body portion extending from the handle assembly, surgical stapling jaws including a staple cartridge assembly and an anvil assembly disposed at a distal end of the body portion, and a staple line reinforcement material (SLRM). At least one of a tissue contacting surface of the staple cartridge assembly and a tissue contacting surface of the anvil assembly incorporates hooks or other engaging features formed in the staple cartridge assembly and/or anvil assembly so that the hooks or engaging features extend from, or recede into, the tissue contacting surface of the staple cartridge assembly and/or anvil assembly. FIGS. 15a through 15e illustrate various shapes for features that can be utilized as hooks or engaging features for engaging a SLRM and retaining the SLRM onto the stapling instrument. The hooks or engaging features are formed as a part of the anvil and/or cartridge surfaces as molded or stamped and/or machined features. Typically, the staple cartridge assembly includes a body molded from a polymeric material, whereas the anvil assembly is formed from one or more parts that are stamped and/or machined from metal. The hooks or engaging features would have geometries that could be made through these part forming methods. Other manufacturing methods can be used.

The SLRM 350 comprises a material having a plurality of pores 352 or fibers 353 that are engaged by the hooks or engaging features 335 at the tissue contacting surface 341 of the staple cartridge assembly 322 and at the tissue contacting surface 342 of the anvil assembly 330. The pores can be formed as apertures in a sheet of material, or recesses, or the pores can comprise openings defined between fibers, threads wires, etc. that makeup the SLRM.

The hooks or engaging features 335 are formed across the tissue contacting surface 341 and/or tissue contacting surface 342. Alternatively, the hooks or engaging features 335 are formed so that the hooks or engaging features 335 are disposed outwardly of linear staple lines, or outwardly and/or inwardly of circular staple lines. The SLRM 350 can be a circular piece of material having a central orifice for accommodating the shafts of a circular stapling instrument. Alternatively, the SLRM 350 is rectangular or oblong in shape for being disposed on a linear surgical stapling instrument. In certain embodiments, the SLRM 350 is applied to the tissue contacting surfaces of the staple cartridge assembly and/or the anvil assembly by pressing the SLRM 350 against the hooks or engaging features 335 on the tissue contacting surfaces. The hooks or engaging features 335 engage the SLRM 350 in the pores 352 or at fibers 353 thereby retaining the SLRM 350 against the tissue contacting surfaces. The SLRM is sized to overlie the tissue contacting surfaces of the staple cartridge assembly and the anvil assembly. The SLRM can be formed from the materials discussed above and the hooks or engaging features, and the pores or fibers of the SLRM, are sized to enable the hooks or engaging features to engage at least some of the pores or fibers in the SLRM to retain the SLRM until the instrument is fired and is removed.

It will be understood that various modifications may be made to the embodiments disclosed herein. For example, the surgical stapling instrument need not apply staples but rather may apply two part fasteners as is known in the art. Further, the length of the linear row of staples or fasteners, or the length or diameter of a circular row of staples or fasteners, may be modified to meet the requirements of a particular surgical procedure. Therefore, the above description should not be construed as limiting, but merely as exemplifications of preferred embodiments. Those skilled in the art will envision other modifications within the scope and spirit of the claims appended thereto.

What is claimed is:

1. A surgical stapling instrument, comprising:
   a handle assembly;
   a body portion extending from the handle assembly;
   surgical stapler jaws including a staple cartridge assembly and an anvil assembly disposed at a distal end of the body portion, each of the staple cartridge assembly and anvil assembly having a tissue contacting surface;
   a staple line reinforcement material;
   a sheet having a first side and a second side, the second side being attached to at least one of the tissue contacting surface of the staple cartridge assembly or the tissue contacting surface of the anvil assembly; and
   a fastener having two parts, the two parts including a hook and a loop, one of the hook or the loop extending from the first side of the sheet, the staple line reinforcement material having the other of the hook or the loop, wherein the hook has a first base end and a second free end, a diameter of the first base end being greater than a diameter of the second free end so that the second free end is relatively flexible, wherein the first base end is stiff relative to the second free end such that a lifting force of at least one of the surgical stapler jaws having the sheet attached thereto is reduced.

2. The surgical stapling instrument according to claim 1, wherein the anvil assembly has staple forming recesses and the cartridge assembly has staple receiving slots.

3. The surgical stapling instrument according to claim 2, wherein the anvil assembly and the cartridge assembly are arranged to form a circular staple line.

4. The surgical stapling instrument according to claim 2, wherein the anvil assembly and the cartridge assembly are arranged to form a linear staple line.

5. The surgical stapling instrument according to claim 1, wherein the staple line reinforcement material is non-woven.

6. The surgical stapling instrument according to claim 1, wherein the staple line reinforcement material is a mesh.

7. The surgical stapling instrument according to claim 1, wherein the staple line reinforcement material has a plurality of pores.

8. The surgical stapling instrument according to claim 7, wherein the sheet has a plurality of hooks that are arranged to engage the plurality of pores.

9. The surgical stapling instrument according to claim 1, wherein the sheet has a plurality of hooks on the first side and an adhesive on the second side, the adhesive being attached to the tissue contacting surface of at least one of the anvil assembly or the staple cartridge assembly, and the staple line reinforcement material has a plurality of loops arranged to engage the plurality of hooks.

10. The surgical stapling instrument according to claim 1, wherein the anvil assembly and the staple cartridge assembly are arranged to form a circular staple line and further comprising a circular knife disposed inwardly of the circular staple line.

11. The surgical stapling instrument according to claim 10, wherein the staple line reinforcement material is circular in shape and has a central orifice.

12. The surgical stapling instrument according to claim 1, wherein the hook is disposed on at least one of the surgical stapler jaws and has a glass transition temperature at or near 37 Centigrade.

13. The surgical stapling instrument according to claim 1, wherein the hook is disposed on at least one of the surgical stapler jaws and has a glass transition temperature and further comprising at least one thermistor for heating the hook to a temperature at or near the glass transition temperature.

14. The surgical stapling instrument according to claim 1, wherein the staple line reinforcement material has a plurality of fibers, at least one of the surgical stapler jaws having the hook, the hook being arranged to engage one or more of the plurality of fibers.

15. The surgical stapling instrument according to claim 1, wherein the staple line reinforcement material is attached to at least one of the tissue contacting surface of the staple cartridge assembly or the tissue contacting surface of the anvil assembly prior to packaging of the surgical stapling instrument.

* * * * *